United States Patent [19]
Atwood

[11] 3,942,952
[45] Mar. 9, 1976

[54] SAMPLE PLATTER MOISTURIZING SYSTEM

[75] Inventor: John G. Atwood, Redding, Conn.

[73] Assignee: The Perkin-Elmer Corporation, Norwalk, Conn.

[22] Filed: Aug. 22, 1974

[21] Appl. No.: 499,586

[52] U.S. Cl. ............... 23/259; 23/253 R; 73/423 A
[51] Int. Cl.² ...................... G01N 1/12; G01N 1/14
[58] Field of Search ................ 23/259, 292, 253 R; 141/130; 73/423 A, 425.6

[56] References Cited
UNITED STATES PATENTS

| | | | |
|---|---|---|---|
| 3,038,340 | 6/1962 | Isreeli | 73/423 A |
| 3,081,158 | 3/1963 | Winter | 23/259 |
| 3,190,731 | 6/1965 | Weiskopf | 23/292 |
| 3,192,968 | 7/1965 | Baruch | 23/259 X |
| 3,449,959 | 6/1969 | Grimshaw | 23/259 UX |

*Primary Examiner*—R. E. Serwin
*Attorney, Agent, or Firm*—S. A. Giarratana; F. L. Masselle; J. K. Conant

[57] ABSTRACT

A moisturizing system for preventing evaporation of samples in a sample platter used in an automatic analysis apparatus in which the sample platter is provided with a channel which can be filled with water and a cover placed over the sample platter with an opening only at the point where samples are drawn from the platter, the platter being rotated relative to this opening to thereby insure that a high level of humidity is maintained over the samples preventing evaporation thereof.

3 Claims, 2 Drawing Figures

SAMPLE PLATTER MOISTURIZING SYSTEM

BACKGROUND OF THE INVENTION

This invention relates to automatic analysis apparatus in general and more particularly to an improved sample platter construction for such apparatus.

In an application of John G. Atwood et al, Ser. No. 499,602 filed Aug. 22, 1974 and assigned to the same assignee as the present invention a completely automatic kinetic analyzer is disclosed. In that analyzer, as with other automatic analyzers, samples to be analyzed are stored in a carousel like sample platter from which they are sequentially drawn out by a diluter probe. The apparatus is capable of running a plurality of different tests on the same sample and thus the samples may reside in the sample platter for a relatively long period of time. If nothing further were done this could result in evaporation of water from these samples and lead to inaccuracies in the testing. Alternatively, it would be required to replace samples after a certain period of time.

Thus, the need for means of maintaining samples in the sample platter in a manner such that the water within the sample is not subject to evaporation becomes evident.

SUMMARY OF THE INVENTION

The sample platter is circular having located around its periphery a plurality of locations for cups containing samples. Adjacent to the cups an angular recess which is filled with water is provided. A cover is placed over the platter covering at least the cups and the annular recess containing the water. The cover rests freely on top of the sample platter and includes means to restrain it from rotation. It contains a single opening for access of a probe into a cup from which a sample is to be drawn. The platter rotates beneath the cover to sequentially position the sample cups in registration with the access opening so that sample can be withdrawn. Through these measures, a high level of humidity is maintained over the samples in the platter thus preventing evaporation of the water contained in the samples. Thus, samples can be maintained in a usable form for a much longer period of time permitting a plurality of tests to be conducted without the need for changing samples.

DETAILED DESCRIPTION OF THE PREFERRED EMBODIMENT

Figure 1:
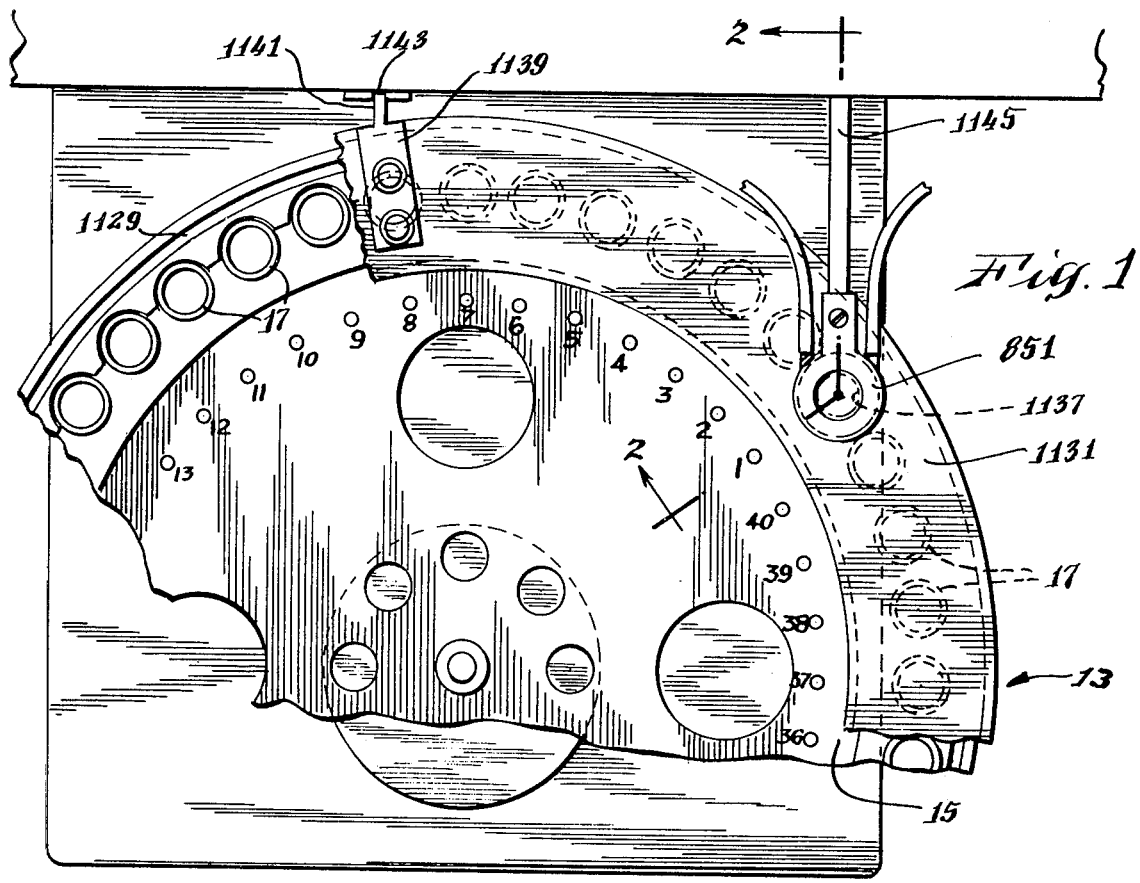
FIG. 1 is a fragmentary plan view of the sample platter of the present invention.
Figure 2:
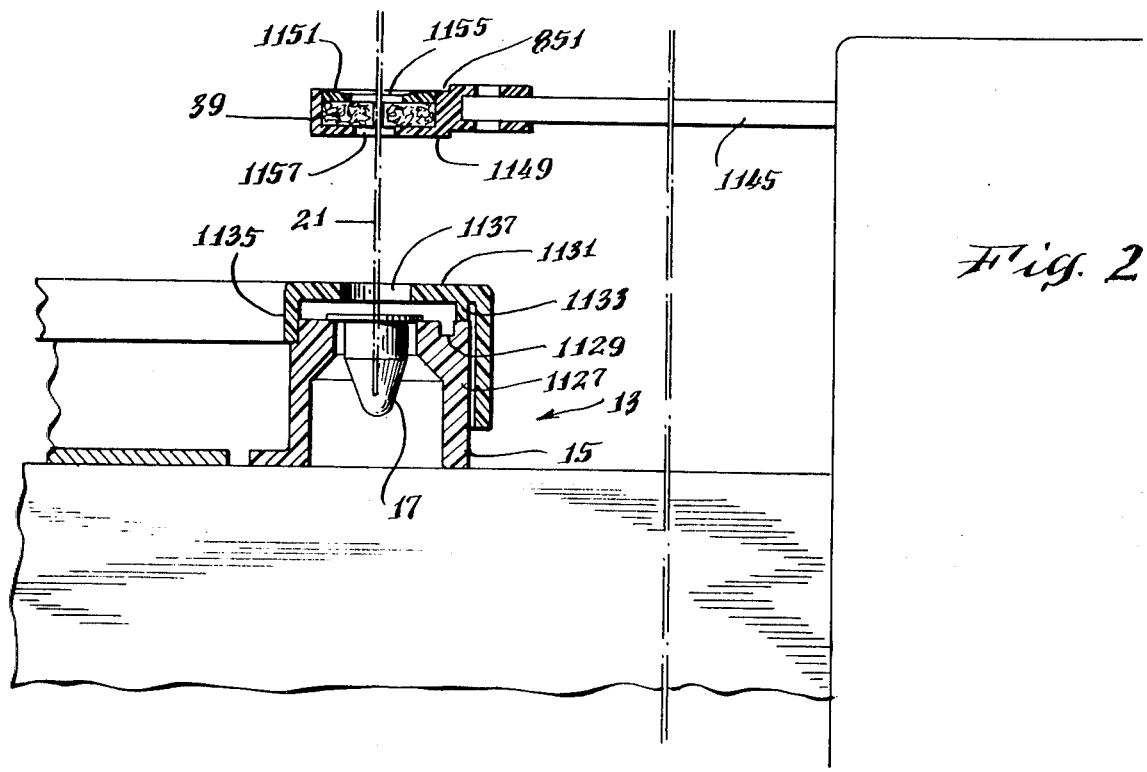
FIG. 2 is a sectional view taken on line 2—2 of FIG. 1.

Referring to the drawings, a sample platter assembly 13 according to a preferred embodiment of the invention is shown to include a circular member or platter 15 having a annular rim 1127 at its outer periphery in which are formed a plurality of apertures, at equiangularly spaced locations, capable of receiving sample cups 17. In operation, sample cups 17 would contain specimens of human serum or other substance to be subjected to analysis. Annular rim 1127 has in its upper surface a concentric annular channel 1129 which may be filled with water. An annular cover 1131 is placed over rim portion 1127 of platter 15. Cover 1131 has downwardly extending annular projections 1133 and 1135 adjoining its outer and inner perimeters, respectively, and resting on suitable correspondingly located portions of the upper surface of platter 15.

A single opening 1137 is provided to cover 1131; the cover is oriented so that opening 1137 is located in alignment with a wiper unit 851 holding a sponge 39 through which a sample pickup probe, represented symbolically at 21, must pass to enter sample cups 17 sequentially positioned below the wiper unit as the platter is rotationally indexed. To establish this orientation of and maintain cover 15 against rotation with the platter 15 on which it rests, a stop member 1139 is provided on the cover at an appropriate location. Stop member 1139 carries a projection 1141 which engages a slot or recess 1143 formed on a stationary part of the apparatus on which the platter assembly is mounted, e.g., on the front of the apparatus housing.

Wiper unit 851 is mounted on a support arm 1145 and includes a base member 1149 and cover member 1151 containing respective aligned central apertures 1157 and 1155 accommodating passage of probe 21 through the wiper unit and sponge 39. The sponge is arranged to contact probe 21 on all sides as it passes through the wiper unit to enter and leave cups 17 as more fully explained in the above-identified copending application.

In operation, sample cups 17 containing the samples to be analyzed are placed in the sample cup locations of the platter, channel 1129 is filled with water and cover 1131 placed in position over the rim 1127 of the platter. The angular orientation of the cover is established by engagement of stop member projection 1141 in recess 1143 and is such that the cover opening 1137 is aligned with wiper unit 851 and the path of probe 21 through the wiper unit to the first sample cup. Platter 15 is then progressively indexed to position each of the sample cups seriatim beneath the wiper unit; meanwhile, the platter cover 1131 remains stationary, its downward projections 1133 and 1135 riding on the mating upper surfaces of the platter. The presence of water in channel 1129, with single opening 1137 the only avenue of egress for water vapor, creates a condition of high humidity within the annular chamber defined between the cover and upper surface of platter rim portion 1127 and overlying and enclosing all of the sample cup locations.

Thus an improved sample platter for serum samples and the like has been shown. Although specific embodiments have been illustrated and described, it will be obvious to those skilled in the art that various modifications may be made without departing from the spirit of the invention which is intended to be limited solely by the appended claims.

What is claimed is:

1. In combination with sampling apparatus including a sample take-up probe, a sample platter having a plurality of sample-cup-holding locations spaced about its periphery and means for rotatably indexing said platter to place said locations sequentially in position for entry of said probe into sample cups in such locations:

a. an annular cover member removably positioned on said platter and defining with a peripheral portion thereof a continuous annular chamber overlying and enclosing said sample cup locations, said cover member containing a single opening into said chamber located to provide access for entry of the sample probe into a cup at a location registering with said opening;
b. means to maintain said cover against rotation with said sample platter, and with said opening in alignment with said probe, whereby sample cups are moved sequentially into registration with said opening as the platter is indexed; and
c. a recess in said platter and open to said chamber for the containment of water to maintain a condition of high humidity within said chamber and thus retard evaporation from the contents of sample cups in said platter locations.

2. In the combination defined in claim 1, said recess being an annular upwardly open channel concentric with said platter and adjacent said sample cup locations.

3. In the combination defined in claim 2, said cover member including annular downward projections at its inner and outer peripheries slidably engaging mating surfaces on the top of said platter.

* * * * *